United States Patent [19]

Russell, Jr. et al.

[11] Patent Number: 4,784,116
[45] Date of Patent: Nov. 15, 1988

[54] CAPSULE FOR INTERSTITIAL IMPLANTS

[75] Inventors: John L. Russell, Jr., Marietta, Ga.; David N. Coggins, Spartanburg, S.C.

[73] Assignee: Theragenics Corporation, Atlanta, Ga.

[21] Appl. No.: 79,766

[22] Filed: Jul. 29, 1987

Related U.S. Application Data

[63] Continuation-in-part of Ser. No. 694,941, Jan. 24, 1985, Pat. No. 4,702,228.

[51] Int. Cl.⁴ ............................................. A61N 5/10
[52] U.S. Cl. .................................................. 128/1.2
[58] Field of Search .................... 128/1.1, 1.2; 424/1.1, 424/1.5

[56] References Cited

U.S. PATENT DOCUMENTS 3,351,049  11/1967  Lawrence ............................ 128/1.2
4,323,055   4/1982  Kubiatowicz ........................ 128/1.2
4,510,924   4/1987  Gray ................................... 128/1.2

Primary Examiner—Edward M. Coven
Attorney, Agent, or Firm—Fitch, Even, Tabin & Flannery

[57] ABSTRACT

A seed for implanting radioactive material within the living body of a recipient which contains radioactive material which emits therapeutic radiation to treat a specific localized area of the recipient's body. A capsule, which sealingly encloses the radioactive material, preventing contact with the recipient's body fluid and tissue, includes a generally cylindrical body portion having a pair of open ends. End members of a wall thickness substantially that of the cylindrical body close the open ends, and include an end wall and a generally tubular skirt portion extending therefrom. The skirt portion and the ends of the cylindrical body are deformably joined together by welding, crimping, peening or other cold flow metal treatment, to form a hermetic seal between the end cap and cylindrical body. Also disclosed is a cylindrical plug-like coupling member which joins the pair of seeds in end-to-end coaxial relationship. Each end of the coupling member is received in a socket-like cavity formed in the hollow interior of one end member.

18 Claims, 2 Drawing Sheets

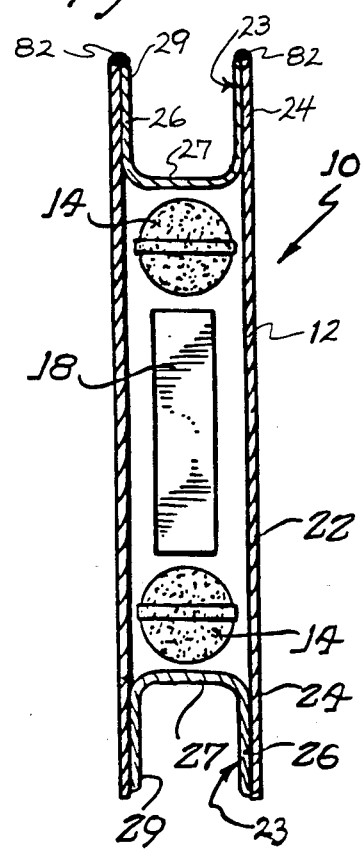
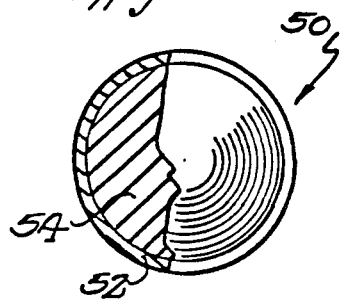
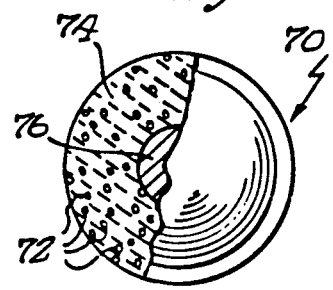

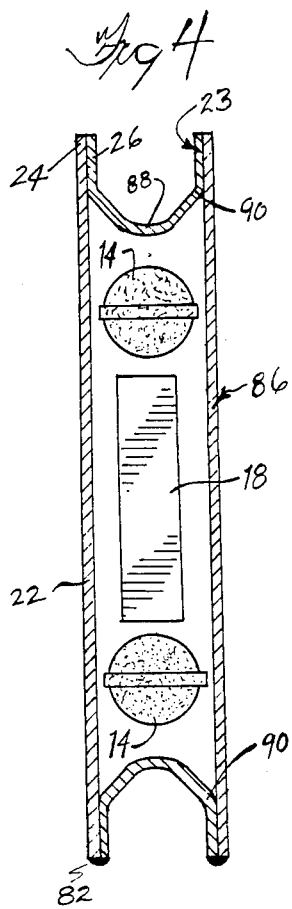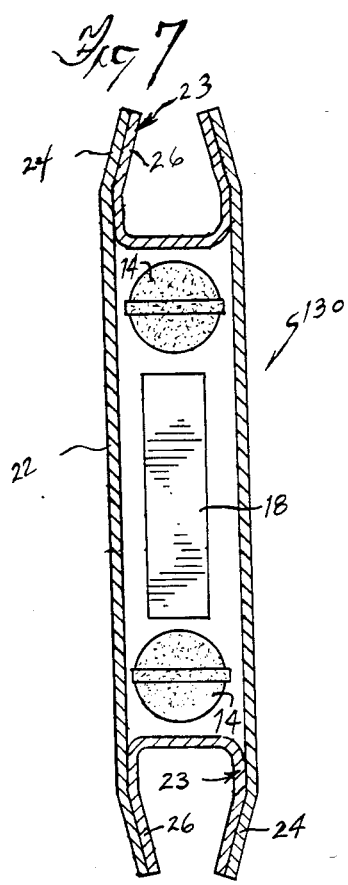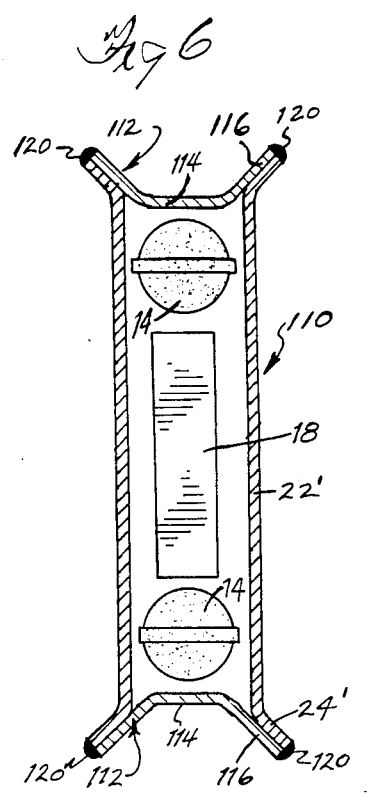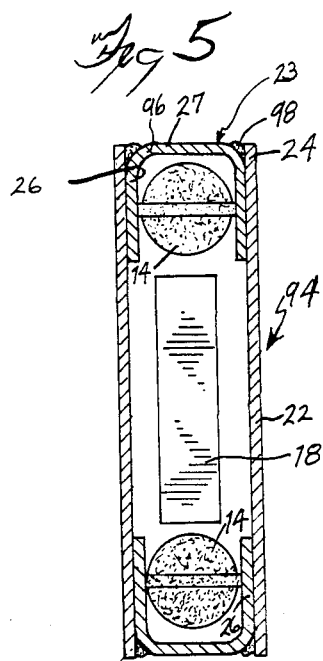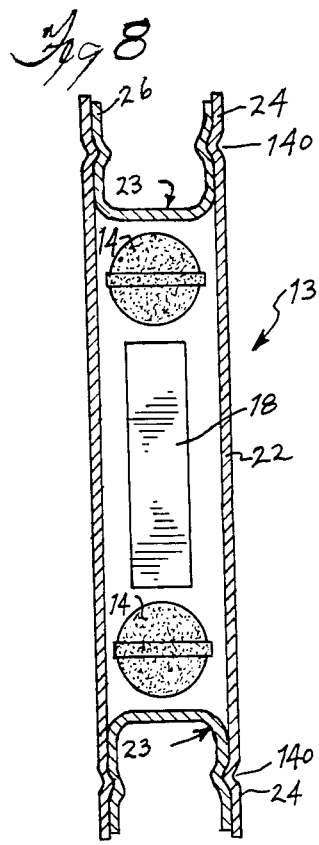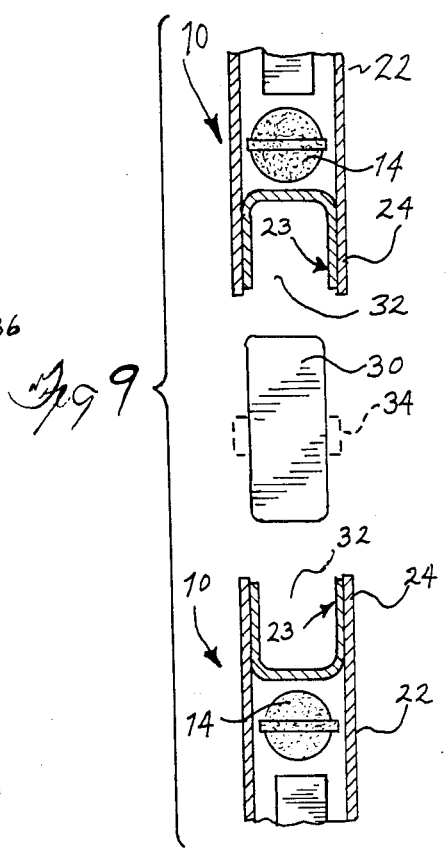

CAPSULE FOR INTERSTITIAL IMPLANTS

RELATED APPLICATIONS

This application is a continuation-in-part of Ser. No. 694,941, filed Jan. 24, 1985, now U.S. Pat. No. 4,702,228, issued Oct. 27, 1987, the disclosure of which is incorporated herein by reference.

BACKGROUND OF THE INVENTION

1. Field of the Invention

The present invention is directed to capsules used in the interstitial implantation of therapeutic radiation sources.

2. Description of the Prior Art

Advantages of interstitial implantation of radiation-emitting material for localized tumor treatment have been recognized for some time now. Interstitially implanted materials concentrate the radiation at the place where this treatment is needed, i.e., within a tumor so as to directly affect surrounding tumor tissue, while at the same time exposing normal tissue to far less radiation than does radiation that is beamed into the body from an external source.

One early implantable radioactive material was gold wire fragments enriched in radiation-emitting gold isotopes, such as gold-198. An advantage of gold wire, for interstitial implantation is that gold is compatible with the body in that it does not degrade or dissolve within the body. Another commonly used implantable material is radon-222.

Materials, such as gold-198 and radon-222, have significant counter-indicating characteristics for interstitial tumor treatment in that they emit relatively penetrating radiation, such as X-rays or gamma radiation of higher energy than is preferred, beta particles or alpha particles. Such materials not only subject the patient's normal tissue to more destructive radiation than is desired but expose medical personnel and other persons coming into contact with the patient to significant doses of potentially harmful radiation.

Capsules for enclosing the radioisotope material so as to form a fully assembled seed offer a number of important advantages. For example, it is important for medical health reasons that the radioisotope materials be isolated so as not to undergo a physical or chemical interaction with body fluids or body tissue while the seed is implanted in a living body. Further, the construction of the capsule should preferably allow rapid and easy insertion in the organ or body part to be treated, with minimal trauma to outer layers of tissue surrounding the affected part. For example, one popular technique for implanting seeds of this type is to inject the seeds into the body using a syringe or similar device. Due to the small size of the capsules, which frequently have outer diameters of the order of 0.5 mm to 0.8 mm, and lengths of the order of 5 mm, this technique is generally preferred.

U.S. Pat. No. 3,351,049 describes seeds including an enclosed outer shell which encases an X-ray-emitting isotope having a selected radiation spectrum. Notably, the isotope material comprises iodine-125 having a radiation spectrum which is quite favorable for interstitial use compared to previously used materials. The encasing shell localizes the radioactive iodine to the tumor treatment site, preventing the migration of iodine to other parts of the body, notably the thyroid, which would occur if bare iodine were directly placed in the tumor site. The use of an encasing shell permits the use of other X-ray-emitting isotopes which would dissolve in the body or present a toxic hazard to the recipient. Capsules containing iodine-125 have been used in treating patients.

U.S. Pat. No. 4,323,055 also discloses a radioactive iodine seed in which the radioisotope material is isolated by a container having sealed ends. As in the above-mentioned '049 patent, details of construction of the encasing shell are not given.

Another capsule construction for encasing radioisotope material is given in U.S. Pat. No. 4,510,924. A tubular body is disclosed having multiple layers, with an intermediate layer comprising the radioisotope material. The ends of the capsule are enclosed by flat disk-like members of a similar multilayer construction, which are welded at their outer edges to interior walls of the multiple-layered tubular body. A hollow interior is defined by the construction, to accommodate gases which may be generated over the operating life of the implanted seed. The multilayer, laminated design is difficult and costly to construct, especially considering the small size of the capsule. Further, the placement of active materials between layered walls of the capsule is not compatible with radioisotope materials that cannot be readily formed into sheet-like configurations. Some materials are more economically produced and function more effectively when configured in a three-dimensional form such as that of a sphere or egg-shaped body. Also, it is frequently desirable to provide an X-ray marker associated with the capsule to aid in the precise citing of the capsule within the body of a recipient. In general, X-ray markers, to be clearly identified, must often be provided in larger quantities than the radioactive material. However, it is generally desirable to incorporate the materials in as compact a package as is possible, a goal difficult, if not impossible, to achieve in the capsule of the above patent.

In order to function effectively, the radiation emitted from the radioisotope material must not be blocked or otherwise unduly attenuated. As indicated above, the small size of therapeutic seeds allows them to be inserted within the organ or tissue to be treated, so as to be totally surrounded thereby. Preferably, it is desirable that the radiation emitted from the radioisotope material have an equal distribution in all directions of emanation, i.e., have an isotropic radial distribution. In particular, it is generally desirable to avoid capsules with end constructions having a greater concentrations of radiation-absorbing material which obstructs the therapeutic radiation required for the successful treatment of affected tissues and organs.

Further, it is generally desirable to provide an economical capsule construction, using a fabrication technique which provides a hermetic seal without adversely affecting the capsule contents by heat or pressure.

SUMMARY OF THE INVENTION

Accordingly, it is an object of the present invention to provide an outer encasing shell which is interstitially implantable in the living body of a recipient, to introduce therapeutic radioactive material in defined localized areas of the recipient's body.

Yet another object of the present invention is to provide an outer encasing shell of the abovedescribed type which is economically manufactured with a minimum number of components, and which minimizes the risk of damage to materials contained within the casing, during fabrication thereof.

Yet another object of the present invention is to provide an outer casing for radiation-emitting materials which exhibits minimum attenuation while allowing an equal distribution of the radiation in all directions of emanation.

These and other objects of the present invention which will become apparent from studying the appended description and drawings are provided in seeds for implanting radioactive material within a living body, which seeds comprise radioactive material and a container sealingly enclosing the radioactive material. The container includes a tubular body of substantially uniform wall thickness having a pair of opposed open ends, enclosed by cap-like end members of wall thickness substantially similar to that of the tubular body. The cap members have an end wall and an annular skirt having a free end depending from the end wall. The end members and the tubular body are deformably joined to each other to form a fluid-tight seal, so as to prevent contact between bodily fluids and the radioactive material in the container.

BRIEF DESCRIPTION OF THE DRAWINGS

In the drawings, wherein like elements are referenced alike,

FIG. 1 is a cut-away view of an implantable radiation-emitting seed, employing a capsule embodying various features of the present invention;

FIGS. 2 and 3 are partially cut-away views of radiation-emitting pellets which may be employed in the seed of FIG. 1;

FIG. 4 shows a seed having an alternative capsule construction, with internal, rounded end caps;

FIG. 5 shows a seed having an alternative capsule construction with inwardly-opening end caps welded to the ends of a tubular body;

FIG. 6 shows a seed having an alternative capsule construction with outwardly flared ends minimizing a shadowing attenuation of radiation emitted from pellets contained within the capsule;

FIG. 7 shows a seed having an alternative capsule construction with inwardly-bent ends;

FIG. 8 shows a seed having an alternative capsule construction with end caps crimpingly engaging the ends of a tubular body; and FIG. 9 is an exploded fragmentary view showing the coupled joinder of a pair of seed capsules, according to one aspect of the present invention.

DETAILED DESCRIPTION OF THE PREFERRED EMBODIMENT

Referring now to the drawings, and especially to FIG. 1, an implantable radiation-emitting seed is illustrated generally at 10 having an outer shell or capsule 12 consisting of a tubular body 22 and end caps 23 closing the open free ends 24 of the tubular body. The end caps have a disk-like end wall 27 from which depends an annular skirt 26 having a free end 29 at the open end of the cap According to one aspect of the present invention, the preferred form of body 24 is that of a hollow cylinder of circular cross-section. The cylindrical shape is preferred for its economical, precise fabrication, and it is compatible for use with syringes for injection of the seeds into their desired intrabody positions. Other shapes are, however, possible. For example, the tubular body 24 may have a non-circular cross-sectional shape, such as that of a square or an oval.

The tubular body 22 and end caps 23 are preferably constructed of the same material, examples of which include beryllium coated with gold, stainless steel, and titanium. The preferred material is ASTM B265-78, grade 2 titanium, a highly purified form of titanium containing only acceptable amounts of elements transmutable to undesirable radioactive isotopes. In particular, the common impurities of iron, cobalt and europium should be minimized. The specific titanium material referred to above, for example, has an iron content less than 0.05%. This preferred material for the shell 11 is particularly advantageous should reactivation of radioisotope material located in the shell be required.

According to one aspect of the present invention, the end caps are deformably joined to the ends of the tubular body. The phrase "deformably joined", as used herein, refers to the mutual deformation of both tube and end caps to form an hermetic or fluid-tight seal therebetween so as to, in part, prevent contact of bodily fluids and tissue with materials carried within a capsule. As will be explained in greater detail herein, three specific examples of such deformable joinders include welding (preferably without use of a rod material), a frictional present-fit engagement, and a crimping engagement sufficient to form a fluid-tight seal.

The seed 10 is implantable at a selected site within a living body for emitting localized X-ray radiation therein. The X-rays are emitted from a pair of pellets 14 of generally spherical shape. The pellets contain an X-ray-emitting or radioactive material that is distributed on or throughout a carrier material, substantially non-shielding of X-rays. The radioactive portion of the pellets is preferably formed of palladium which is substantially enriched in palladium-102 and which has been activated (transmuted) by exposure to neutron flux to contain a small, but significant, fraction of X-ray-emitting palladium-103. In the X-ray-emitting pellets 14 depicted in FIG. 1, the enriched palladium material is distributed in a carrier or base material substantially non-absorbing of X-rays, such as highly purified aluminum. When constructed in spherical form, pellets 14 preferably have a diameter of 0.6 mm, a size which provides between about 0.01 and about 0.05 mg of Pd-102-enriched palladium for each pellet.

In order to ensure that the X-ray-emitting seeds 10 implanted within a tumor are properly positioned and distributed therein so as to adequately subject all of the tumorous tissue to therapeutic X-ray radiation doses, it is desirable to visualize the implanted seeds by external means. Generally, this is accomplished by X-ray examination using an X-ray beam from a source external to the body. Accordingly, a rod-shaped marker 18 is interposed between the two pellets 14. The marker 18 is formed of X-ray opaque material to provide a means of visualizing seed 10 after the seed has been implanted within the body of a recipient. Although the marker is highly shielding of the low-energy X-rays emitted by the palladium-103 in the pellets 14, the disposition of the opaque marker 18 between two X-ray-emitting pellets serves to assure that a substantially isotropic angular distribution of X-rays is emitted from the seeds.

Referring to FIG. 2, the activated palladium-102 designated by numeral 52 is coated on a spherical palladium base 54 which acts as an X-ray marker. The numeral 50 generally indicates this pellet construction.

Referring now to FIG. 3, an alternative pellet construction 70 includes a spherical center 76 of high Z material, such as lead, rhodium, gold or tungsten, which serves as an X-ray marker. Surrounding center 76 is a dispersion of Pd-102-enriched palladium particulates 72 suspended in a layer 74 of low-shielding ceramic base material. Various seed constructions other than those illustrated in FIGS. 2 and 3 are possible.

Referring again to FIG. 1, the outer shell or capsule 12 is constructed from a three-piece assembly which generally includes a right circular cylinder or tubular body 22 having open free ends 24 which are enclosed by end caps 23. The generally outwardly-opening end caps have disk-like end walls 27 from which depend right-circular cylindrical skirts 26. The free ends 29 of skirts 26 are welded to the tubular free ends 24 to form a welded joinder 82. For purposes of clarity, only the upper end of the shell 12 of FIG. 1 is shown in a fully assembled and welded condition. According to one aspect of the present invention, it is preferred that the welding employed to join the end caps to the tubular body does not use a flux or a rod material for filling or otherwise bridging gaps or interstices between the joined members. Rather, the welding techniques employed cause the material of the joined members to flow together forming a weld alloy.

According to other aspects of the present invention, the welded joinder forms a continuous, generally circular seal between the tubular body and end cap members. Welded techniques which may be employed, include laser beam, electron beam, and tungsten inert gas (TIG) techniques. The free ends 24 of body 22 and the skirt portion 26 of end cap 23 provide a heat-dissipating fin-like portion remote from the radiation-emitting pellets 14. This construction, in addition to ensuring the proper axial alignment between end cap and tubular body, presents a weld portion of thin-gauge members at a convenient point for carrying out the welding operation.

As pointed out above, the finished diameter of seed 10 is approximately 0.8 mm, with tubular ends and end caps having substantially uniform thicknesses equal approximately to one-tenth of the seed diameter, or 0.05 mm. Accordingly, the welded joinder at the ends of seed 10 must be carefully controlled to avoid destroying the configurations of either the tubular body ends or the end caps. It is important to maintain these configurations for a variety of reasons. As indicated above, the seeds are implanted in a living body of a recipient using perforate insertion or injection techniques. Since the seeds 10 must pass smoothly through the needle of a syringe or the like insertion device, the outer diameter and surface of the capsule 12 should be smooth and well-defined, and in particular, should not be so oversized as to prevent insertion in the desired manner. Further, the internal diameter and generally circular configuration of end caps 23 should be preserved if another object of the present invention is to be achieved, namely, the end-to-end joinder of multiple seeds 10 using plug-like coupling members, as will be described below with reference to FIG. 9.

As will now be explained in greater detail, FIGS. 4-8 illustrate alternative embodiments of capsules constructed according to various features of the present invention, each having end caps deformably joined to a tubular body. Preferably, the tubular bodies of these alternative arrangements comprise right-circular cylinders having lengths approximately ten times their outer diameter. Preferably, to minimize trauma to a patient incurred during insertion, and to provide a localized control of emitted radiation, the capsules of the present invention typically have an outside diameter of about 0.8 mm, but generally no more than 1 mm. For ease of illustration, the various capsule constructions are shown encasing radiation-emitting pellets 14 and X-ray markers 18 of the same general type described above with respect to FIG. 1.

Referring now to FIG. 4, a seed is illustrated having a capsule or shell 86 generally identical to the shell 12 described above with respect to FIG. 1, except that the end caps 23 include generally concave end walls 88 having a pointed, rounded nose, which aids in insertion of the end caps within the free ends of the tubular body 22. In general, it is desired that the end caps 23, and especially their depending skirt 26, be slightly oversized compared to the internal diameter of the tube ends 24. This facilitates a stable positioning of the end cap during welding. The outer, free edges of the end cap skirt and tubular body may be welded as indicated in the bottom of FIG. 4. However, a non-welded deformable joinder providing a hermetic seal is also possible with the construction of FIG. 4, as indicated at the upper end thereof, which is not welded.

According to other aspects of the present invention, a 5 to 10 percent oversize in diameter is preferred, so as to provide approximately a cold weld hermetic seal by taking advantage of the ability of the rather thin tubular bodies to expand a limited amount upon insertion of the end cap. For example, a titanium tubular body having an outside diameter of 0.032 inch ±0.001 inch and a wall thickness of 0.002 inch ±0.0002 inch can be expanded in diameter by an amount of 0.003 inch to provide an enhanced cold weld and frictional engagement with the end cap, particularly with an end cap having a skirt of length at least 75 percent of the diameter of the tubular body. The rounded nose portion provided by the concave end walls 88 further aids in the ready insertion of the end caps which centers the end cap and provides a wedging action so as to facilitate the high pressure insertion of the end cap with attendant cold metal flow. It is preferred in this connection, that the diameter of skirt 26 adjacent the concave end 88 be 5 percent smaller in diameter than the internal diameter of tubular body 22, and that the end caps have a 2° to 5° taper in their upper portion, where swelling engagement is initiated, generally where the end cap and skirt meet.

Due to the 10 percent oversize of the major portion of the skirt 26, compared to the inner diameter of tubular shell 22, the frictional engagement and pressure generated between the skirt and the free ends 24 of body 22 generates a preliminary deformed joinder of the end cap skirt and tubular body, resulting in what approximates a cold weld uniting. In some circumstances, this deformable cold weld joinder is sufficient to provide the required hermetic seal, particularly if the ends of the tubular body and the end caps are manufactured with close tolerances. If further sealing is required, the cold weld deformable joinder enhances a subsequent weld operation by reducing the gaps and voids between the end cap and tubular body members, an important feature, especially where welding flux or rod (filler) material is not employed in the welding operation. In general, a non-welded deformable joinder may be preferred when there is risk of impairing pellets 14 by overheating or where radiation embrittlement of a weld portion may result from subsequent exposure to continuous radiation from pellet 14 or from reactivation of the pellet.

If the effective length of the seed must be reduced for any reason, the arrangement of FIG. 5 may be employed, wherein a seed 94 is identical to that of FIG. 1, except that the tubular body 22 is shortened, and the end caps 23 are reversed so as to open inwardly, toward the interior of the shell. Since the skirts 26 of the end caps are inaccessible, the welding operation is performed between the free end 24 of the tubular body and the circular edge 96 where the end wall 27 meets the skirt 26. In FIG. 5, the numeral 98 is directed to the weld area where material from the tubular body free end 24 and the edge portion 96 of end cap 23 flow together. As mentioned above, the arrangement of FIG. 5 may be used when an axially compact configuration is required, however, the arrangement is generally not preferred, compared to the arrangements of FIGS. 1 and 4, for example, because the welding operation in effect removes material from portions of the end cap adjacent the end wall 27. However, it is within the skill of those in art to carefully complete the welding operation without weakening or perforating the end cap and thus allow subsequent intrusion of bodily fluids or tissue within the interior of the shell. Although, as pointed out above, the use of a welding rod or filler material is not preferred, titanium material may be used for the configuration of FIG. 5.

Turning now to FIG. 6, an alternative welded type deformable joinder between the end caps and tubular body is illustrated in a seed generally indicated at 110. The tubular body 22, radiation-emitting pellets 14 and X-ray marker 18 are as described above. The free ends 24' are, in contrast to the above-described arrangements of FIGS. 1 and 4, outwardly flared, preferably along radii originating at the center of spherical pellet 14. The end cap construction of FIG. 6, generally indicated at 112, has a disk-like end wall 114 which, as illustrated in FIG. 6, can be considerably smaller than the internal diameter of the tubular body. The skirt 116 of end cap 12 has a general frusto-conical configuration and is sized for intimate engagement or interesting with outwardly-flared free ends of the tubular body. The free ends of the tubular body and the free ends of the end cap skirt 116 are welded at 120, using any of the methods described above, to provide the desired seal between end cap and tubular body member. One advantage of the construction of FIG. 6 is that walls of the tubular body and end cap skirt lie along a radial line of the spherical pellet 14, thereby presenting minimum shadowing or blocking of radiation emanating therefrom.

Unlike the other arrangements presented herein, the seed 110 does not have a smooth outer surface. Nonetheless, the amount of increase in the outside diameter of the fully formed seed is not great compared to that of FIG. 1, for example. In the preferred embodiment, the increase in diameter is slightly over 50 percent of that of the diameter of the tubular body, a condition which does not prohibit the implantation of seed 110 by syringe or perforate injection methods. Further, in some instances it is desired to ensure that the seed does not migrate from its desired position when planted in the living body of a recipient. This is particularly true of those seeds which are permanently implanted. The outwardly-extending cone-like structures formed at each end of the shell of seed 110 aid in anchoring the seed in its desired position, so as to resist any undesired dislocation.

Referring now to FIGS. 7 and 8, two other examples of non-welded deformable joinder constructions are given. Referring first to FIG. 7, a seed assembly generally designated at 130 is substantially identical to that described above with respect to FIG. 1, except that the free ends 24 of the tubular shell 22 and the skirts 26 of end caps 23 have been radially inwardly deformed in either a swaging or a peening operation to cause a cold flow of metal material between these two members, so as to form the desired hermetic seal.

Turning now to FIG. 8, a seed 136 is shown which originally is also substantially identical to the arrangement of FIG. 1, containing radiation-emitting pellets 14 and an X-ray marker 18. However, unlike the arrangement of FIG. 1, the end caps 23 are not welded to the free ends 24 of the tubular body. Instead, the end cap skirts 26 and the tubular body free ends 24 are mutually deformed along a radially-inward compression ring or band 140. Preferably, the ring of inward deformation is achieved in a conventional Magneforming process or with a crimping die. In either event, the deformation results in a flow of body and end cap skirt material in the ring-like region 140 to provide the desired hermetic seal to prevent contact between the contents of the seed and the body tissue of the recipient.

Referring now to FIG. 9, a coupling member 30 is adapted to join pairs of seeds in end-to-end relationship. The coupling member is dimensioned to fit within the blind cylindrical apertures 32 formed in the interior of the outwardly-extending end caps 23. Coupling members 30 are preferably cylindrical in configuration, having an outside diameter sized for significant frictional engagement with the open end of a fully formed seed 10. Preferably, each end of the coupling member 30 has an axial length sufficient to not only provide the frictional retention forces desired, but also to align the axes of the seeds being joined in coaxial relationship.

When rigid coaxial alignment of seeds is desired, the coupling member 30 may be formed of titanium or other biocompatible metal, preferably of low Z material so as to interfere as little as possible with the radiation emitted from the seeds. Coupling members 30 may also be made from a biocompatible plastic, thereby allowing a limited flexing of movement between joined seeds. This latter feature is particularly advantageous when the needle used for insertion of the seeds in the body of a recipient is curved so as to define a pathway around various parts of the patient's body.

As illustrated, the coupling member 30 has a generally smooth, continuous outer surface. If desired, one or more spacer members, such as the spacer members 34 indicated in phantom in FIG. 9 can be added to the major body portion of the plug member. The spacer members 34 can comprise one or more projections spaced about the central portion of the coupling member body, or may comprise a continuous ring or band of material. In either event, the spacer members 34 would contact the free ends of the seeds 10, adjacent the free ends of the end cap skirts and tubular bodies. In the preferred embodiment, for seeds having an approximate diameter of 0.8 mm, and a length of approximately 5 mm, the length of spacers 34 (as measured in the axial direction of the seed) is approximately 0.5 mm, but can also be quite longer, preferably, ranging between 2 and 14 mm, so as to provide a separation between opposing radiation-emitting pellets, thereby reducing the blocking of pellet radiation as might occur when the free ends of adjacent seeds are very close to each other.

It will thus be seen that the objects hereinbefore set forth may readily and efficiently be attained and, since certain changes may be made in the above construction and different embodiments of the invention without departing from the scope thereof, it is intended that all matter contained in the above description or shown in the accompanying drawings shall be interpreted as illustrative and not in a limiting sense. For example, although all of the seeds have been illustrated as having identical caps at each end, which is preferred but not mandatory because one end of the seed is normally closed before the radioactive material is inserted. Thus, it might be possible to form a tubular body of seamless construction having one end closed, using forming methods similar to those employed in making the popular aluminum beverage cans.

What is claimed is:

1. A seed for implanting radiation-emitting material within a living body, comprising:
    radiation-emitting material; and
    a container means for sealingly enclosing said radiation-emitting material, including a tubular body of substantially uniform wall thickness having at least one open end and an end cap of wall thickness not substantially greater than that of said tubular body closing said open end, said end cap having an end wall and a generally tubular skirt portion depending from the periphery of said end wall and terminating in a free end, said skirt portion being at least partially received in the open end of said tubular body so as to engage said tubular body, said skirt portion and said tubular body interfitting and joined to each other to form a fluid-tight seal, so as to prevent contact between bodily fluids and said radiation-emitting material in said container.

2. The seed of claim 1 wherein said skirt portion extends from said end wall in a direction longitudinally of said tubular body toward a medial portion along the length of said tubular body.

3. The seed of claim 2 further comprising a second end cap at least partially disposed within and joined to another end of said tubular body.

4. The seed of claim 3 wherein the tubular body has a circular cross section and the end wall has a circular edge which is welded to said tubular body.

5. The seed of claim 1 wherein said skirt portion extends away from said end wall in a direction longitudinally along said tubular body toward said open end.

6. The seed of claim 5 wherein the skirt portion crimpingly engages said tubular body.

7. The seed of claim 5 wherein said free end of the skirt is joined by a weld to an end edge of the open end of said tubular body.

8. The seed of claim 5 wherein the skirt portion of said end cap has a generally cylindrical shape defining a plug-receiving socket, the seed further comprising a plug-like coupling member having a first end engagingly received in said socket and a second end engagingly receivable in a socket of another seed.

9. The seed of claim 5 wherein the skirt portion of said end cap and the open end of said tubular body receiving said skirt portion are deformed toward the longitudinal axis of said tubular body so as to form the fluid-tight seal therebetween.

10. The seed of claim 5 wherein said skirt portion has a generally frustoconical shape opening away from the periphery of said end wall, and the open end of said tubular body has a flair extending away from the longitudinal axis of said tubular body.

11. A seed for implanting radiation-emitting material within a living body, comprising:
    radiation-emitting material;
    a tubular body enclosing said radiation-emitting material, said tubular body having a substantially uniform wall thickness and at least one open end; and
    a closure member having a wall of thickness not substantially greater than that of said tubular body, said wall of said closure member having an end portion and a generally tubular skirt portion depending from the periphery of the end portion and terminating in a free end; and
    said closure member being interfitted within the end of said tubular body and joined thereto by welding to form: a fluid-tight seal, so as to prevent contact between bodily fluids and said radiation-emitting material disposed within said tubular body.

12. The seed of claim 11 wherein the skirt portion of said closure member wall extends from said wall end portion in a direction longitudinally along said tubular body toward a medial portion of said tubular body.

13. The seed of claim 11 wherein the skirt portion of said closure member wall extends away from said wall end portion in a direction longitudinally along said tubular body toward the open end.

14. The seed of claim 11 wherein said skirt portion has a generally frustonical shape opening away from the periphery of said end wall, and the open end of said tubular body has a flair extending away from the longitudinal axis of said tubular body.

15. A seed for implanting radiation-emitting material within a living body, comprising:
    radiation-emitting material;
    a tubular body enclosing said radiation-emitting material, said tubular body having a substantially uniform wall thickness and at least one open end; and
    a closure member having a wall of thickness not substantially greater than that of said tubular body, said wall of said closure member having an end portion and a generally tubular skirt portion depending from the periphery of the end portion and terminating in a free end; and
    said closure member being interfitted within the end of said tubular body and joined thereto by mechanical deformation to form a fluid-tight seal, so as to prevent contact between bodily fluids and said radiation-emitting material disposed within said tubular body.

16. The seed of claim 15 wherein the skirt portion of said closure member wall extends from said wall end portion in a direction longitudinally along said tubular body toward a medial portion of said tubular body.

17. The seed of claim 15 wherein the skirt portion of said closure member wall extends away from said wall end portion in a direction longitudinally along said tubular body toward the open end.

18. The seed of claim 15 wherein said skirt portion has a generally frustoconical shape opening away from the periphery of said end wall, and the open end of said tubular body has a flair extending away from the longitudinal axis of said tubular body.

* * * * *